(12) United States Patent
Miyazawa et al.

(10) Patent No.: US 7,976,814 B2
(45) Date of Patent: *Jul. 12, 2011

(54) FULLERENE DERIVATIVE FINE WIRE AND ITS MANUFACTURING METHOD

(75) Inventors: Kun'ichi Miyazawa, Ibaraki (JP); Tadatomo Suga, Ibaraki (JP); Tadahiko Mashino, Tokyo (JP)

(73) Assignee: National Institute For Material Science, Ibaraki (JP)

( * ) Notice: Subject to any disclaimer, the term of this patent is extended or adjusted under 35 U.S.C. 154(b) by 694 days.

This patent is subject to a terminal disclaimer.

(21) Appl. No.: 10/574,920

(22) PCT Filed: Oct. 6, 2004

(86) PCT No.: PCT/JP2004/015089
§ 371 (c)(1),
(2), (4) Date: Jun. 12, 2006

(87) PCT Pub. No.: WO2005/035480
PCT Pub. Date: Apr. 21, 2005

(65) Prior Publication Data
US 2007/0053822 A1  Mar. 8, 2007

(30) Foreign Application Priority Data
Oct. 7, 2003  (JP) .................................. 2003-348667

(51) Int. Cl.
*C01B 31/02*  (2006.01)
(52) U.S. Cl. ............... 423/445 B; 423/447.2; 423/447.1
(58) Field of Classification Search .................. 423/445
See application file for complete search history.

(56) References Cited

U.S. PATENT DOCUMENTS

| 6,890,505 B2 * | 5/2005 | Miyazawa et al. ......... 423/447.2 |
| 2004/0208816 A1 * | 10/2004 | Mashino .................. 423/445 B |
| 2008/0003165 A1 * | 1/2008 | Miyazawa et al. ........ 423/445 B |

OTHER PUBLICATIONS

M. T. Beck et al, "The weak interaction between C60 and molecular iodine in solution," Russian Chemical Bulletin, vol. 45, No. 8, 2129-2130(1996).*
Guldi, et al. Langmuir 2000, 16, 1311-1318.*
Miyazaki, Koichi et al., "Analysis of $C_{60}$ Derivative Nano-whisker by Transmission Electronmicroscopy", *Electron Microscopy*, vol. 38, Supplement 1, p. 160 (Jun. 7, 2003).

* cited by examiner

*Primary Examiner* — Melvin C Mayes
*Assistant Examiner* — Yun Qian
(74) *Attorney, Agent, or Firm* — Wenderoth, Lind & Ponack, L.L.P.

(57) ABSTRACT

The invention presents a fullerene derivative fine wire composed of basic component unit of fullerene derivative, being made of acicular crystal of fullerene derivative, as a fine wire showing high crystallinity and semiconductor performance.

3 Claims, 10 Drawing Sheets

FULLERENE DERIVATIVE FINE WIRE AND ITS MANUFACTURING METHOD

TECHNICAL FIELD

The present invention relates to a fullerene derivative fine wire and its manufacturing method. More particularly, the invention relates to a fullerene derivative fine wire composed of fullerene derivative only, or fullerene derivative and fullerene neatly arrayed at high crystallinity, and a method of manufacturing the same.

BACKGROUND ART

Recently, ultrasmall devices such as micromachines are highly noticed. To realize such ultrasmall devices, it requires a conductive fine wire for feeding electricity to an electrical driving mechanism. However, a general metal fine wire has its crystal grain boundary formed by crystallization, it has problems in increase of electric resistance by impurities segregated in the grain boundary, rupture at grain boundary, and increase in surface roughness in the grain boundary. Accordingly, attention has been paid to carbon fine wire as precise conductive fine wire in an ultrasmall device.

On the other hand, fullerene is a general term of carbon allotrope of carbon atoms bonded like a soccer ball or rugby ball, and its synthesis has been reported by many researchers. The fullerene molecule is largely different in shape from the graphite having a flat bonding surface in layer, and it is a great feature that it has a curvature in bonging surface of fullerene molecule. The fullerene can control the strength, rigidity, electrical resistance, optical property, or magnetic property by enclosing the metal compound or organic compound, overlapping in concentric sphere, or introducing a functional group in the surface, and when a fine wire of fullerene linked regularly and at high crystallinity is obtained, it is expected to be useful as nanoconductive material.

Among fullerene derivatives, the molecule having the highest rate of curvature is $C_{60}$. $C_{60}$ was discovered in 1985 (H. W. Kroto, J. R. Heath, S. C. O'Brien, R. F. Curl and R. E. Smailey; Nature, 318 (1985) 162-163), and its mass synthesis method was found in 1990 (W. Kratschmer, Lowel D. Lamb, K. Fostiropoulos and D. R. Huffman; Nature, 347 (1990) 354-357). Recently, an acicular substance composed of this $C_{60}$ is drawing attention, and it is reported that toluene solution of $C_{60}$ is obtained (for example, S. Ogawa, H. Furusawa, T. Watanabe and H. Yamamoto, "Observation of condensed structure of $C_{60}$ assembled from solution," Journal of Physics and Chemistry of Solids, 61 (2000) 1047-1050). In these methods hitherto reported, $C_{60}$ deposits from toluene solution of $C_{60}$, and an amorphous acicular substance of about 20 mm is obtained in about 6 months, and the growth speed was far from practical level in order to manufacture one-dimensional substance composed of fullerene, in particular wire material.

In the meantime, an associated body obtained by adding fullerene lean solvent to solution of fullerene monomer was disclosed (Japanese Patent Application Laid-Open No. 10-1306). But this associated body is a granular substance having fullerene monomer associated by van der Waals force, and it was neither crystal nor fine wire.

Another method was reported for obtaining $C_{60}$ acicular substance by evaporating solution of dissolving $C_{60}$ in 95 wt. % hexane and 5 wt. % benzene, in a range from room temperature to 80° C. (Y. Tosida, Jpn. J. Appl. Phys. 1992: 31, L505), but the obtained acicular crystal had a very rough surface and it was polycrystalline. Hence, it cannot be used as conductive material.

The present inventors have previously reported fullerene fine wire as a new conductive material by discovering a method of preparing fullerene fine wire by liquid-liquid interface deposition method using fullerene solution (Japanese Patent Application Laid-Open No. 2003-1600 (U.S. patent application Ser. No. 10/125,333)). However, this material has lattice defect of high density (dislocation, lamination defect), and the properties as semiconductor were not so high as expected.

The present invention is devised in the light of the above background, and it is hence an object thereof to solve the problems of the prior art, and present a fine wire having high crystallinity and semiconductor performance in the basis component unit of fullerene derivative, and a method of manufacturing the same easily.

DISCLOSURE OF INVENTION

To solve the problems, it is a first aspect of the invention to present a fullerene derivative fine wire composed of acicular crystal of fullerene derivative, and a second aspect to present a fullerene derivative fine wire composed of acicular crystal of fullerene derivative and fullerene.

It is a third aspect of the invention to present a fullerene derivative fine wire of which fullerene derivative is selected from the group consisting of diethyl ester malonate derivative of $C_{60}$, N-methylpyrrolidine derivative of $C_{60}$, ferrocene derivative of $C_{60}$, and platinum derivative of $C_{60}$, and a fourth aspect to present a fullerene derivative fine wire of which acicular crystal is monocrystalline.

It is a fifth aspect of the invention to present a manufacturing method of fullerene derivative fine wire composed of acicular crystal of fullerene derivative, being a manufacturing method of fullerene derivative fine wire comprising at least the steps of preparing a solution by dissolving fullerene derivative in a first solvent, adding a second solvent of lower fullerene derivative dissolving ability than the first solvent to this solution, forming a liquid-liquid interface between the solution and the second solvent, and depositing the fullerene derivative fine wire on the liquid-liquid interface.

It is a sixth aspect of the invention to present a manufacturing method of fullerene derivative fine wire composed of acicular crystal of fullerene derivative and fullerene, being a manufacturing method of fullerene derivative fine wire comprising at least the steps of preparing a solution by dissolving fullerene derivative and fullerene in a first solvent, adding a second solvent of lower fullerene derivative dissolving ability than the first solvent to this solution, forming a liquid-liquid interface between the solution and the second solvent, and depositing the fullerene derivative fine wire on the liquid-liquid interface.

It is a seventh aspect of the invention to present a manufacturing method of fullerene derivative fine wire of which fullerene derivative is selected from the group consisting of diethyl ester malonate derivative of $C_{60}$, N-methylpyrrolidine derivative of $C_{60}$, ferrocene derivative of $C_{60}$, and platinum derivative of $C_{60}$, an eighth aspect to present a manufacturing method of fullerene derivative fine wire of which first solvent is at least one kind selected from the group consisting of benzene, toluene, xylene, hexane, and pentane, and a ninth aspect to present a manufacturing method of fullerene derivative fine wire of which second solvent is selected from the group consisting of methyl alcohol, ethyl alcohol, n-propyl alcohol, isopropyl alcohol, butyl alcohol, and pentanol.

BEST MODE FOR CARRYING OUT THE INVENTION

The fullerene derivative fine wire of the invention is a fine wire made of acicular crystal of fullerene derivative only, or fullerene derivative and fullerene. The concept of "fine wire" includes "whisker", "nano whisker", "nano fiber", and "wire".

In the fullerene derivative fine wire of the invention, the fullerene derivative is composed of various fullerenes ($C_{60}$, $C_{70}$, $C_{82}$, etc.), together with various functional groups bonded or various metals incorporated therein. More specifically, any one of fullerenes $C_{60}$, $C_{70}$, $C_{82}$ is combined with one or more of hydroxyl radical, alkoxy radical, aryl radical, acyl radical, acetyl radical, carboxyl radical, alkoxy carbonyl radical, halogen radical, cyano radical, amino radical, imino radical, nitro radical, mercapto radical, alkylthio radical, sulfonyl radical, acyl radical or other substituents, or may further incorporate transition metal or rare earth metal. In particular, preferred examples are diethyl ester malonate derivative of $C_{60}$, N-methylpyrrolidine derivative of $C_{60}$, ferrocene derivative of $C_{60}$, and platinum derivative of $C_{60}$. The fullerene may be selected from various fullerenes ($C_{60}$, $C_{70}$, $C_{82}$, etc.).

In the fullerene derivative fine wire composed of acicular crystal of fullerene derivative and fullerene, the combination of fullerene derivative and fullerene is not particularly specified, and the blending ratio is not limited. For example, it may be properly adjusted in a range of 99.9:0.1 to 0.1:99.9.

In the fullerene derivative fine wire of the invention, the fullerene derivative (and fullerene) is neatly arrayed as clear from the embodiments given below, and an acicular crystal is formed. The acicular crystal may be monocrystalline. The monocrystalline of fullerene derivative or the monocrystalline of fullerene derivative and fullerene are discovered in the present invention for the first time in the world, and the growth axis is in the filling direction of highest density of fullerene derivative (or fullerene derivative and fullerene) molecule.

Also in the fullerene derivative fine wire of the invention, the acicular crystal may form a polycrystal, especially in fullerene derivative fine wire of large diameter. The "polycrystal" is a structure of bundling of several fine wires of monocrystalline of fullerene derivative or fullerene derivative and fullerene.

The acicular crystal may be a laminated body of thin plates formed by laminating thin plates composed of fullerene derivative (or fullerene derivative and fullerene). The thickness or shape of thin plates of fullerene is not particularly specified. For example, slabs of fullerene acicular crystal of 1 to 50 nm in thickness may be stacked up by 1 to 100 pieces, or combinations of thin plates different in thickness may be stacked up by 1 to 100 sets.

Therefore, the fullerene derivative fine wire of the invention is crystallographically different from the hitherto known polymer or associated body of fullerene (patent document 1), and the structure and properties are evidently different from the composition of introducing derivatives into them.

The fullerene derivative fine wire of the invention may be formed in various diameters or lengths, and can be obtained in diameter of several units of nm or more and length of several hundreds of μm to several cm. Hence, the aspect ratio (length/diameter) of fullerene derivative fine wire of the invention ranges over hundreds, and it may be called fullerene derivative nano whisker.

The fullerene derivative fine wire of the invention has a large aspect ratio, and is higher in strength and has anisotropy as compared with powder crystal made of known fullerene alone. Fullerene and fullerene derivative are small in coefficient of friction, and these crystals have no crystal grain boundary, and hence the surface roughness is extremely small at atomic level. Having a smooth surface of low coefficient of friction, it can be used as lightweight conductive fine wire, and in the aspects of reduction of weight and surface roughness, problems of conventional metal fine wires can be solved. Further, the fullerene derivative fine wire is capable of controlling its chemical properties and electrical characteristics by properly selecting the types and number of substituents in the fullerene derivative, or substances to be incorporated in the fullerene.

Therefore, the fullerene derivative fine wire of the invention is expected to be used and applied in wide fields including the electric industry, electronic industry, automobile industry, machine industry, space and aircraft industry, pharmaceutical industry, and energy industry. More specifically, it is considered to be used as ferrodielectric ceramics polymer, piezoelectric element, self-lubricating ceramics polymer, insulating material, semiconductor material, pharmaceuticals, optical device, material for hydrogen storage device, etc.

The fullerene derivative fine wire of the invention can be polymerized by high pressure hot press to form polymerized fullerene derivative wire, or hot-pressed together with ceramics at high pressure to form polymerized fullerene derivative wire-ceramics compound.

The invention also presents a manufacturing method of fullerene derivative fine wire composed of acicular crystal of fullerene derivative. Specifically, the method comprises at least:

(1) a step of preparing a solution by dissolving fullerene derivative (or fullerene derivative and fullerene) in a first solvent, and adding a second solvent of lower dissolving ability of fullerene derivative (or fullerene derivative and fullerene) than the first solvent to this solution, (2) a step of forming a liquid-liquid interface between the solution and the second solvent, and (3) a step of depositing the fullerene derivative fine wire on the liquid-liquid interface.

Thereby a fullerene derivative fine wire is obtained.

In the manufacturing method of fullerene derivative fine wire of the invention, the fullerene derivative as the material is composed of various fullerenes ($C_{60}$, $C_{70}$, $C_{82}$, etc.), together with various functional groups bonded or various metals incorporated therein. More specifically, any one of fullerenes $C_{60}$, $C_{70}$, $C_{82}$ is combined with one or more of hydroxyl radical, alkoxy radical, aryl radical, acyl radical, acetyl radical, carboxyl radical, alkoxy carbonyl radical, halogen radical, cyano radical, amino radical, imino radical, nitro radical, mercapto radical, alkylthio radical, sulfonyl radical, acyl radical or other substituents, or may further incorporate transition metal or rare earth metal. In particular, preferred examples are diethyl ester malonate derivative of $C_{60}$, N-methyl pyrrolidine derivative of $C_{60}$, ferrocene derivative of $C_{60}$, and platinum derivative of $C_{60}$. The fullerene may be selected from various fullerenes ($C_{60}$, $C_{70}$, $C_{82}$, etc.).

The combination of fullerene derivative and fullerene is not particularly specified, and the blending ratio is not limited. For example, it may be properly adjusted in a range of 99.9:0.1 to 0.1:99.9.

In the invention, the first solvent for dissolving fullerene derivative (or fullerene derivative and fullerene) is not particularly specified as far as it can dissolve fullerene derivative (or fullerene derivative and fullerene). A solvent may be used alone, or two or more solvents may be mixed. In particular, solvents high in dissolving ability of fullerene derivative (and fullerene) preferably include nonpolar solvents. Specific examples include at least one hydrocarbon solvent selected from the group consisting of benzene, toluene, xylene, hexane, and pentane. As the first solvent, toluene, benzene, xylene, and hexane are particularly preferred.

At this time, the fullerene derivative (and fullerene) solution may be either saturated solution or unsaturated solution, but the saturated solution is preferred. By using the saturated solution, the fullerene derivative fine wire deposits efficiently. The first solvent may include additives, if necessary, for enhancing the dissolving ability of fullerene derivative (and fullerene), so far as deposition of fullerene derivative fine wire is not disturbed.

In the manufacturing method of fullerene derivative fine wire of the invention, the second solvent may be any type of solvent system different from the first solvent for dissolving fullerene derivative (or fullerene derivative and fullerene), and one solvent may be used alone, or two or more solvents may be mixed. Such second solvent may be any lean solvent small in dissolving ability of fullerene derivative (and fullerene), and polar solvents are preferred as solvent system specifically. Specific examples are methyl alcohol, ethyl alcohol, n-propyl alcohol, isopropyl alcohol, butyl alcohol, pentanol and other alcoholic solvents, and also ethylene glycol and other polyhydric alcohols. The second solvent may also include additives as an auxiliary agent for promoting deposition of fullerene derivative fine wire.

In the manufacturing method of fullerene derivative fine wire of the invention, a liquid-liquid interface is formed between the fullerene derivative (or fullerene derivative and fullerene) solution and the second solvent, and by making use of this liquid-liquid interface, fullerene derivative fine wire composed of fullerene derivative (or fullerene derivative and fullerene) deposits from the fullerene derivative (or fullerene derivative and fullerene) solution.

Such liquid-liquid interface can be formed by using the first solvent and second solvent of mutually not mixing systems. The liquid-liquid interface is not required to isolate the first solvent and second solvent permanently, but they may be mixed in the midst of standing still. Therefore, a particularly preferred combination of solvents is toluene for the first solvent and isopropyl alcohol for the second solvent.

Further, the liquid-liquid interface can be also formed by adding the second solvent slowly to the fullerene derivative (or fullerene derivative and fullerene) solution. This technique is particularly effective when the first solvent and second solvent are composed of solvent systems partly mixing with each other. The method of adding the second solvent slowly to the fullerene derivative (or fullerene derivative and fullerene) solution includes a method of pouring the second solvent along the wall of the container of the fullerene derivative (or fullerene derivative and fullerene) solution (wall method). Or a method of dropping the second solvent slowly into the container of the fullerene derivative (or fullerene) solution (dropping method) may be applied.

In such manufacturing method of fullerene derivative fine wire of the invention, conditions can be set properly, such as type, purity and amount of starting materials such as fullerene derivative or fullerene, type and amount of first solvent and second solvent, type and temperature of additives, material and size of container, and the like. For example, it can be manufactured at room temperature (about 21° C.), preferably −20° C. to 75° C., or more preferably 10° C. to 30° C. The container is preferred to be transparent container so that the state of deposition of fullerene derivative fine wire can be monitored easily. The container may be shielded from light for the purpose of preventing strong photochemical reaction of fullerene, but it has been found by the inventors that fullerene derivative fine wire of high crystallinity can be obtained without shielding from light. The size of the container is not particularly specified, but usually an easy-to-handle bottle of about 20 mm in diameter is used, or a beaker of 100 mL or the like may be used when manufacturing a large quantity of fullerene derivative fine wire. Preferably, a bottle with a lid for preventing evaporation of solvents (for example, vial bottle) is used. The material of the container is not particularly specified as far as it hardly reacts with the first solvent and second solvent, and is excellent in stability and durability, and an easily available glass is used preferably.

The fullerene derivative fine wire manufactured in the manufacturing method of fullerene derivative fine wire of the invention can be separated from the solution in a general separation process, such as filtering or centrifugal separation. The obtained fullerene derivative fine wire is crushed into proper size by grinder or other means, and a fullerene derivative fine wire of homogeneous grain size and length may be obtained.

The invention is specifically described below by presenting exemplary embodiments. It must be noted however that the invention is not limited to these examples alone, but may be changed and modified in various forms.

Exemplary Embodiments

Embodiment 1

In a toluene solution saturated with $C_{60}$, a solution containing about 5% of $C_{60}$ diethyl ester malonate derivative ($C_{60}$ [$C(COO_2H_5)_2$]) was added and mixed, and about 2 mL was poured into 5 mL glass vial bottle.

Using a pipet, (a) isopropyl alcohol (IPA) was poured slowly along the wall of the vial bottle, or (b) dropped slowly, and a liquid-liquid interface was formed. The vial bottles were shielded from light and stored still for 10 days at 21° C.

Figure 1:
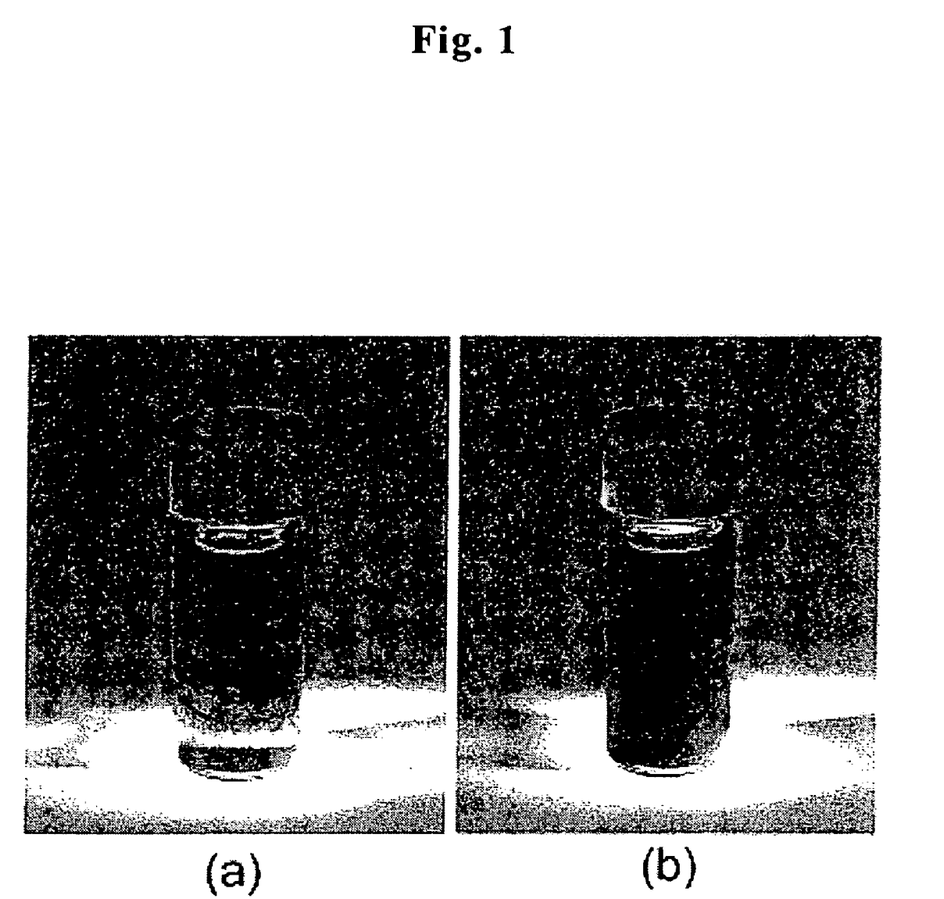
FIG. 1 is a drawing replacing photographs showing fullerene derivative fine wire composed of $C_{60}$ diethyl ester malonate derivative and $C_{60}$ manufactured in an embodiment of the invention. In the drawing, (a) shows the second solvent injected slowly along the wall of the vial bottle into the solution of fullerene derivative and fullerene, and (b) shows the second solvent dropped slowly into the solution of fullerene derivative and fullerene.
Figure 2:
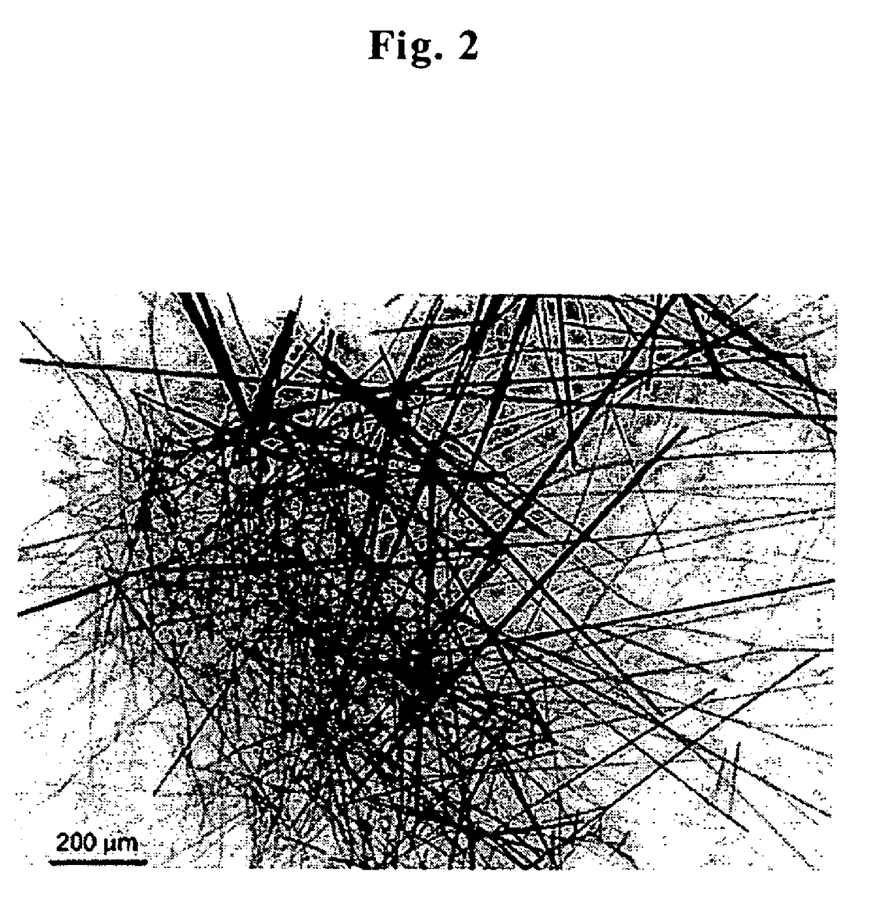
FIG. 2 is a microscopic image of fullerene derivative fine wire obtained by injecting the second solvent slowly along the wall of the vial bottle into the solution of fullerene derivative and fullerene in an embodiment of the invention.

A photograph of obtained fullerene derivative fine wire is shown in FIG. 1. A microscopic image of the fullerene derivative fine wire in FIG. 1 (a) is shown in FIG. 2. A fullerene derivative fine wire of diameter of sub-micron and length of hundreds of µm, and a fullerene derivative fine wire of diameter of several µm to hundreds of µm and length of 1 mm were recognized.

Figure 3:
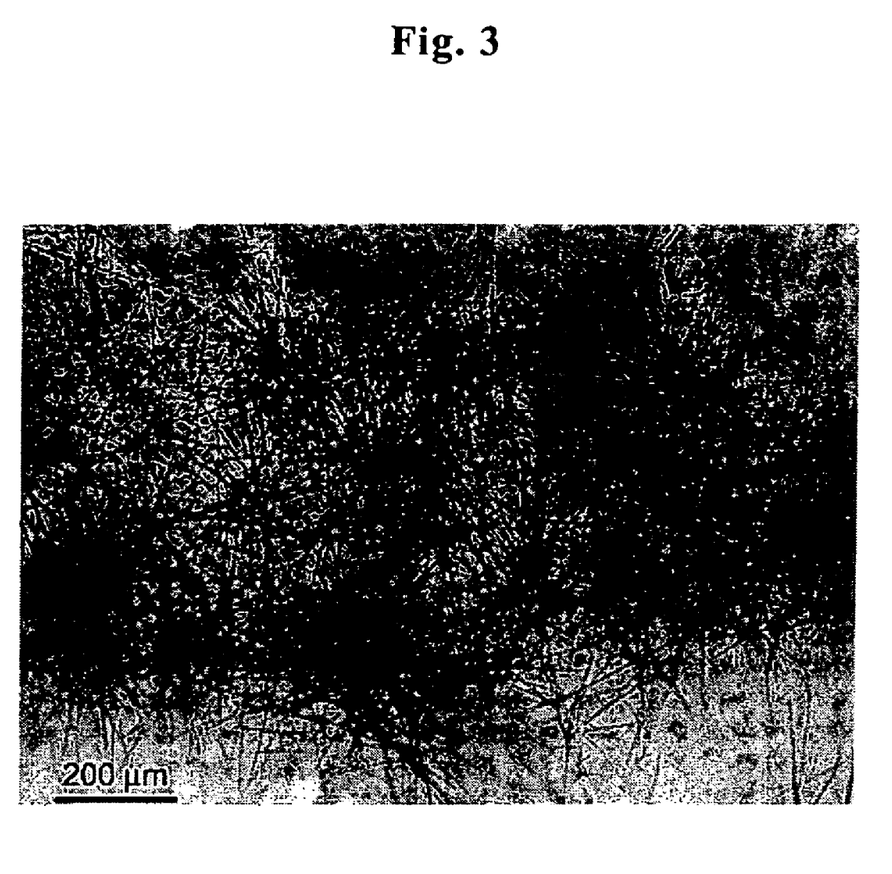
FIG. 3 is a microscopic image of fullerene derivative fine wire obtained by dropping the second solvent slowly into the solution of fullerene derivative and fullerene in an embodiment of the invention.

In the microscopic image of fullerene derivative fine wire of FIG. 1 (b) (FIG. 3), a fullerene derivative fine wire was recognized.

Figure 4:
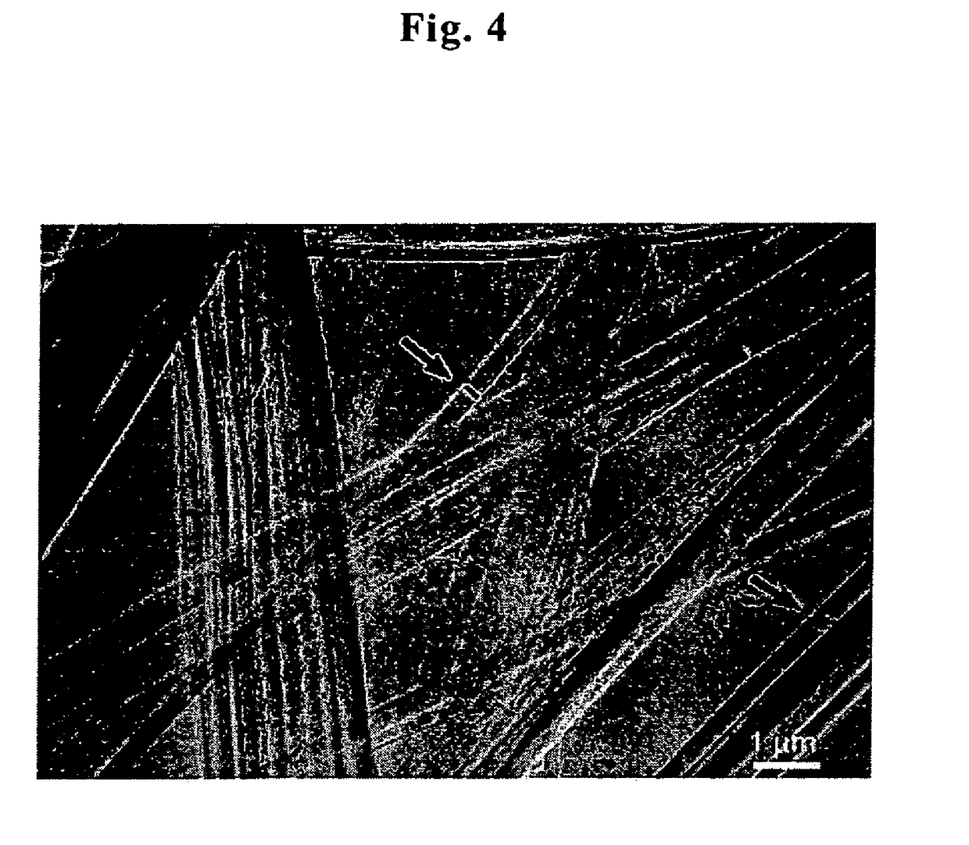
FIG. 4 is an image of transmission electron microscope (TEM) of fullerene derivative fine wire obtained in an embodiment of the invention. The arrow shows extinction fringe.

A transmission electron microscopic (TEM) image of obtained fullerene derivative fine wire is shown in FIG. 4. At the position indicated by arrow, a continuous extinction fringe was noted, and the fullerene derivative fine wire is confirmed to be a monocrystalline. Hence, the obtained fullerene derivative fine wire is a monocrystalline of fullerene derivative and fullerene, and the aspect ratio is over 100 in FIG. 2 and FIG. 3, and it is known to be so-called nano fiber.

As known from a high resolution transmission electron microscopic (HRTEM) image of fullerene derivative fine wire containing $C_{60}[C(COOC_2H_5)_2]$ (FIG. 5), in the fullerene derivative fine wire, $C_{60}$ cages are arrayed neatly and a high crystallinity was proved.

Figure 5:
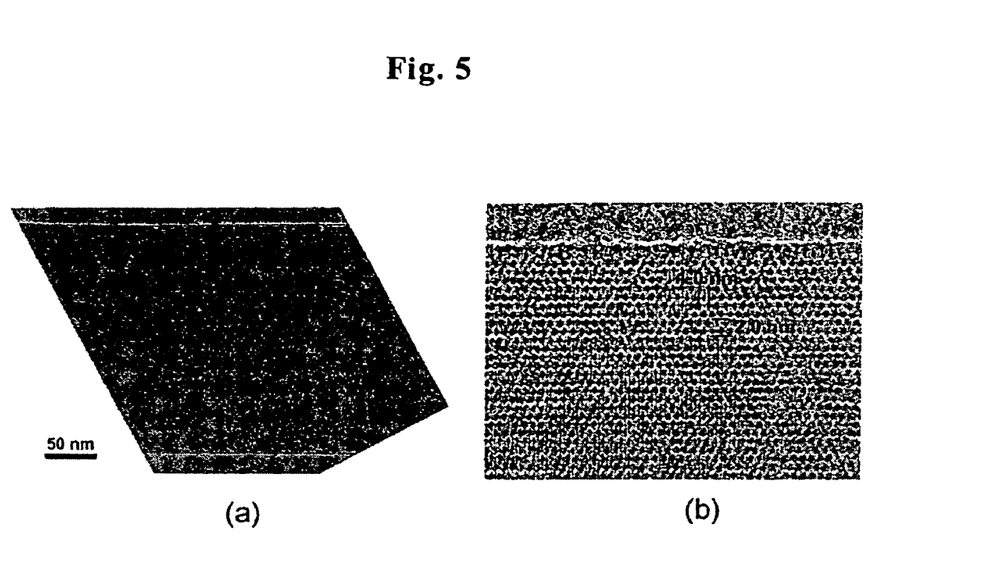
FIG. 5 is an image of high resolution transmission electron microscope (HRTEM) of fullerene fine wire containing $C_{60}$ [$C(COOC_2H_5)_2$] manufactured in an embodiment of the invention. In the diagram, (b) is a magnified view of (a).

Further, in its fast Fourier transform (FFT) image, the lattice constants were analyzed. By assuming a body-centered tetragonal system, lattice constants a=0.999 nm, c=2.026 nm were obtained. In the studies made so far, lattice constants of $C_{60}$ monocrystalline nano whisker have been known to be a=0.962 nm, c=1.50 nm (non-patent document 5), and hence the large increase of c-axis and large increase of a-axis in the fullerene derivative fine wire are suggested to be due to solid solution of fullerene derivative having functional groups.

Embodiment 2

In a glass vial bottle, in a toluene solution saturated with $C_{60}$ diester malonate derivative ($C_{60}$ [$C(COO_2H_5)_2$]), isopropyl alcohol was added slowly, and a liquid-liquid interface of toluene saturated solution (lower layer)/isopropyl alcohol (upper layer) was formed, and by letting stand for 1 week at about 21° C., a fullerene derivative fine wire composed of ($C_{60}$ [$C(COO_2H_5)_2$]) only was obtained.

Figure 6:
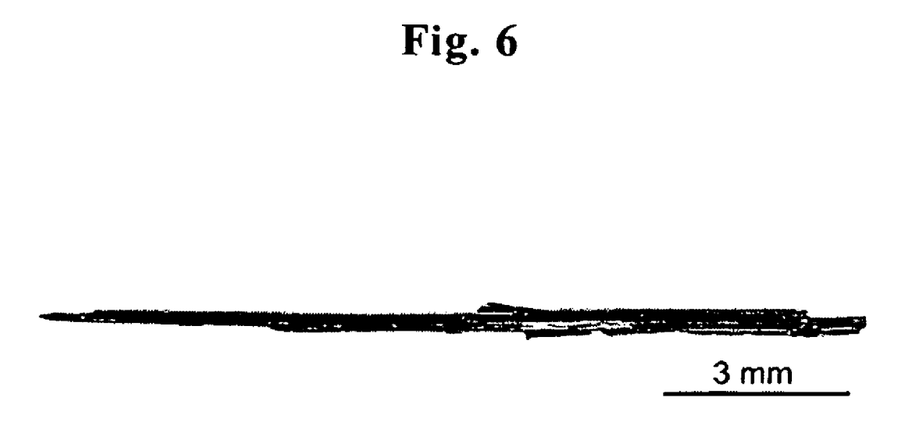
FIG. 6 is an optical microscopic image of fullerene derivative fine wire composed of $C_{60}$ diethyl ester malonate derivative obtained in an embodiment of the invention.
Figure 7:
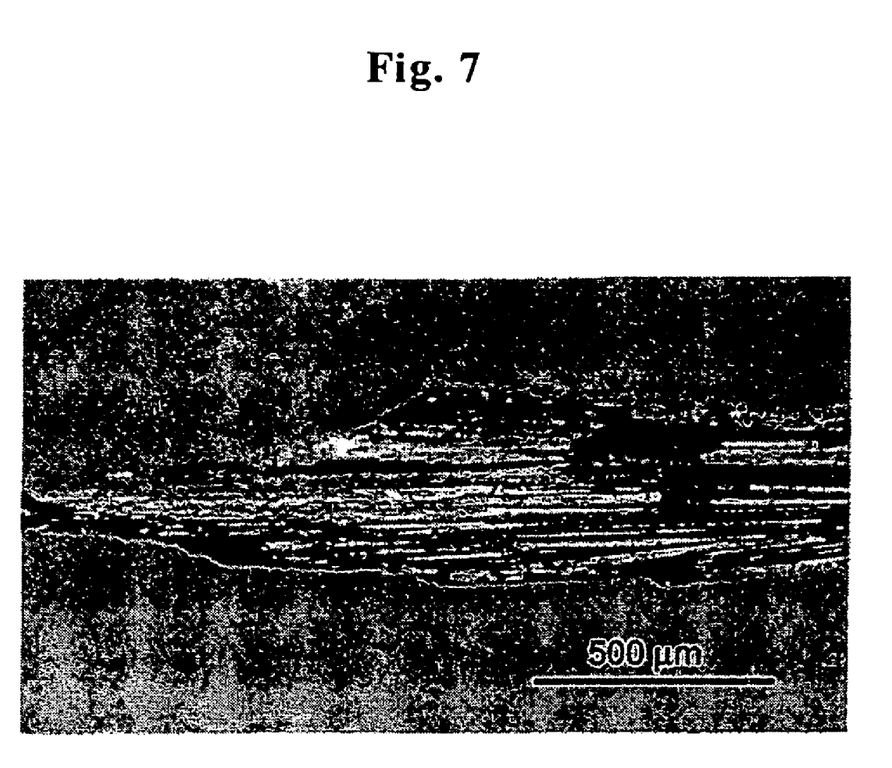
FIG. 7 is a magnified view of the optical microscopic image of FIG. 6.
Figure 8:
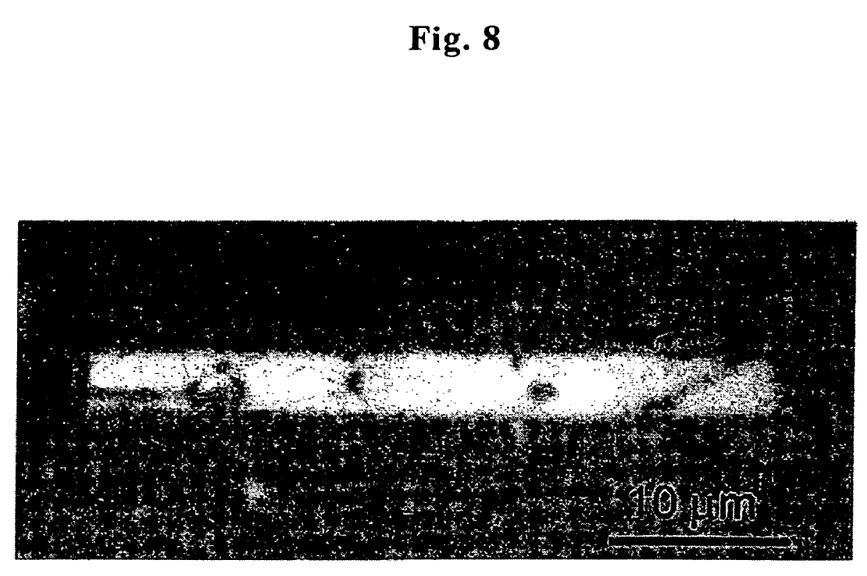
FIG. 8 is an optical microscopic image of fullerene derivative fine wire composed of $C_{60}$ diethyl ester malonate derivative obtained in an embodiment of the invention.

An optical microscopic image of the obtained fullerene derivative fine wire is shown in FIG. 6, and its magnified view in FIG. 7. The fullerene derivative fine wire was confirmed to grow to a length of as much as 1 mm or more. The fullerene derivative fine wire is identified to be composed of acicular crystal having a laminated structure of thin plates. Among obtained crystals, the diameter was less than 5 µm in some as shown in FIG. 8.

Figure 9:
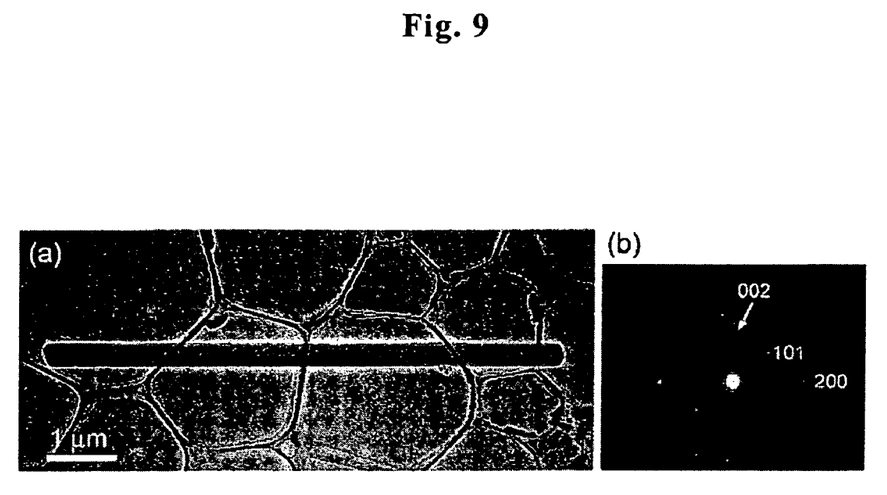
FIG. 9 is a TEM image of fullerene derivative fine wire composed of $C_{60}$ diethyl ester malonate derivative obtained in an embodiment of the invention. In the diagram, (a) is a TEM image, and (b) is a selected area electron diffraction pattern (SAEDP).

FIG. 9 is a TEM image of fullerene derivative fine wire composed of ($C_{60}$ [$C(COO_2H_5)_2$]). As clear from the selected area electron diffraction pattern (SAEDP), the ($C_{60}$[$C(COO_2H_5)_2$]) fine wire was a monocrystalline. Lattice constants were a=0.98 nm, c=1.55 nm.

Figure 10:
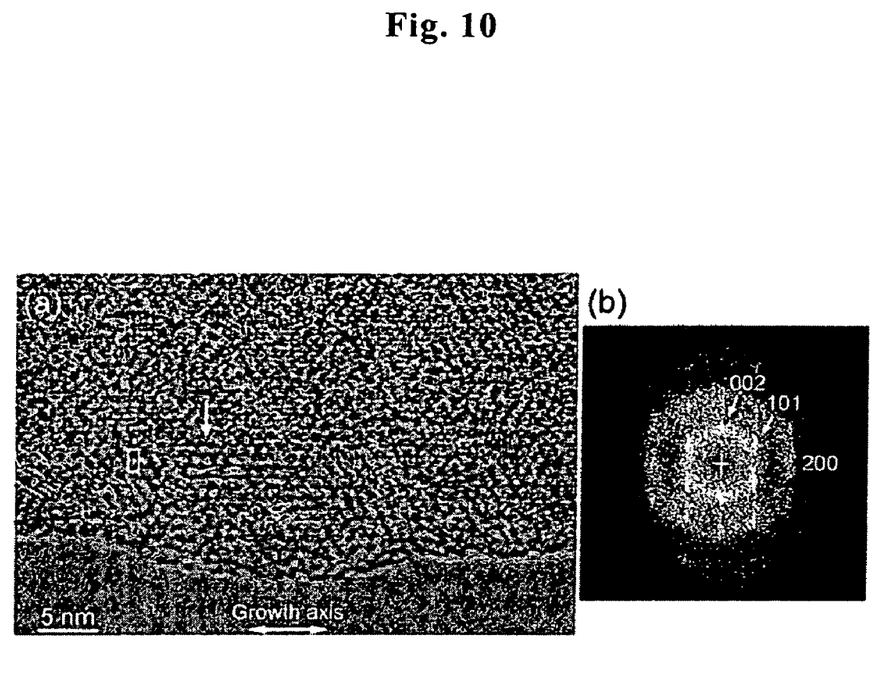
FIG. 10 is a high resolution image of fullerene derivative fine wire composed of $C_{60}$ diethyl ester malonate derivative having lattice constants of a=0.98 nm, c=1.68 nm obtained in an embodiment of the invention. In the diagram, (a) is a TEM image, and (b) is a fast Fourier transform (FFT) image.

FIG. 10 is a high resolution image of ($C_{60}[C(COO_2H_5)_2]$) fine wire having lattice constants of a=0.98 nm, c=1.68 nm. As indicated by arrow, ($C_{60}$ [$C(COO_2H_5)_2$]) is confirmed to be arrayed neatly. From the value of lattice constant a, it is clarified that the $C_{60}$ cage of derivative molecule is filled up densely with $C_{60}$ without allowing intervening malonic acid atomic group.

INDUSTRIAL APPLICABILITY

As described herein, the invention presents a fullerene derivative fine wire composed of basic component unit of fullerene derivative, and showing high crystallinity and semiconductor performance, and a method of manufacturing the same easily.

What is claimed is:

1. A manufacturing method of fullerene derivative fine wire composed of acicular crystal of a diethyl ester malonate derivative of $C_{60}$ and fullerene $C_{60}$, being a manufacturing method of fullerene derivative fine wire comprising at least the steps of preparing a solution by dissolving fullerene $C_{60}$ in a first solvent, mixing a solution containing the diethyl ester malonate derivative of $C_{60}$ with the solution, adding a second solvent of lower fullerene derivative and fullerene dissolving ability than the first solvent to this mixed solution, forming a liquid-liquid interface between the solution and the second solvent, and depositing the fullerene derivative fine wire on the liquid-liquid interface.

2. The manufacturing method of fullerene derivative fine wire of claim 1, wherein the first solvent is at least one kind selected from the group consisting of benzene, toluene, xylene, hexane, and pentane.

3. The manufacturing method of fullerene derivative fine wire of claim 1, wherein the second solvent is selected from the group consisting of methyl alcohol, ethyl alcohol, n-propyl alcohol, isopropyl alcohol, butyl alcohol, and pentanol.

\* \* \* \* \*